US012806317B2

(12) United States Patent
Kuramoto

(10) Patent No.: US 12,806,317 B2
(45) Date of Patent: Nov. 24, 2026

(54) ENDOSCOPIC SUBMUCOSAL INJECTION MATERIAL

(71) Applicant: FUJIFILM Corporation, Tokyo (JP)

(72) Inventor: Mamoru Kuramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 405 days.

(21) Appl. No.: 18/537,704

(22) Filed: Dec. 12, 2023

(65) Prior Publication Data

US 2024/0115774 A1 Apr. 11, 2024

Related U.S. Application Data

(63) Continuation of application No. PCT/JP2022/018074, filed on Apr. 18, 2022.

(30) Foreign Application Priority Data

Jun. 16, 2021 (JP) ................................ 2021-100417

(51) Int. Cl.
*A61L 31/04* (2006.01)

(52) U.S. Cl.
CPC ......... *A61L 31/042* (2013.01); *A61L 2430/34* (2013.01)

(58) Field of Classification Search
CPC ........................... A61L 31/042; A61L 2430/34
See application file for complete search history.

(56) References Cited

U.S. PATENT DOCUMENTS

| | | | | |
|---|---|---|---|---|
| 6,319,260 | B1 | 11/2001 | Yamamoto | |
| 8,293,220 | B2 * | 10/2012 | Kinoshita | A61K 8/39 424/70.28 |
| 11,458,229 | B2 | 10/2022 | Yano et al. | |
| 12,403,224 | B2 | 9/2025 | Yano et al. | |
| 2011/0178184 | A1 | 7/2011 | Kaneko et al. | |
| 2018/0280587 | A1 | 10/2018 | Yano et al. | |
| 2021/0283317 | A1 | 9/2021 | Yano et al. | |
| 2025/0177616 | A1 | 6/2025 | Yano et al. | |
| 2025/0303028 | A1 | 10/2025 | Yano et al. | |

FOREIGN PATENT DOCUMENTS

| | | |
|---|---|---|
| CN | 102112496 | 6/2011 |
| CN | 108136077 | 6/2018 |
| EP | 2783709 | 10/2014 |
| JP | 2001192336 | 7/2001 |
| JP | 2014188054 | 10/2014 |
| JP | 2017506208 | 3/2017 |
| WO | 2013077357 | 5/2013 |
| WO | 2015054208 | 4/2015 |
| WO | 2020105668 | 5/2020 |

OTHER PUBLICATIONS

Okubo,. International Journal of Pharmaceutics 575 (2020) 118845 (Year: 2020).*

Ikeda, WO2004073713A1, machine translation. (Year: 2004).*

"International Search Report (Form PCT/ISA/210) of PCT/JP2022/018074", mailed on Jun. 14, 2022, with English translation thereof, pp. 1-7.

"Written Opinion of the International Searching Authority (Form PCT/ISA/237) of PCT/JP2022/018074", mailed on Jun. 14, 2022, with English translation thereof, pp. 1-6.

Toshio Shimamoto et al., "The characteristics of Sangelose and its application", Pharm Tech Japan, vol. 26, 2010, with English translation thereof, p. 1-p. 12.

Toshiyuki Morisawa et al., "Cellulose nanofiber dispersion as a new submucosal injection material for endoscopic treatment: preliminary experimental study", Endoscopy International Open, Apr. 2020, E623-E627.

Ryohei Hirose et al., "Identification of the critical viscoelastic factor in the performance of submucosal injection materials", Materials Science and Engineering: C, vol. 94, Oct. 2018, pp. 909-919.

Takuma Yoshida et al., "Viscosity: An important factor in predicting the performance of submucosal injection materials", Materials & Design, vol. 195, Jul. 2020, pp. 1-11.

Jun Nakamura et al., "Efficacy of Sodium Carboxymethylcellulose Compared to Sodium Hyaluronate as Submucosal Injectant for Gastric Endoscopic Submucosal Dissection: A Randomized Controlled Trial", Digestion, Feb. 2021, pp. 753-759.

"The First Office Action of China Counterpart Application", issued on Apr. 25, 2026, with English translation thereof, p. 1-p. 11.

* cited by examiner

*Primary Examiner* — Layla D Berry
(74) *Attorney, Agent, or Firm* — JCIPRNET

(57) ABSTRACT

An endoscopic submucosal injection material containing: water; and a polysaccharide represented by Formula (1) is provided:

(1)

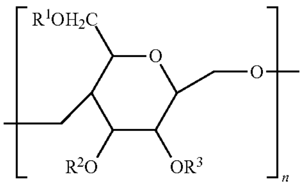

wherein in Formula (1), $R^1$, $R^2$, and $R^3$ each independently represent a hydrogen atom or the like; n represents an integer of 100 to 100,000; k represents 0 or 1; m represents an integer of 1 to 10; j represents an integer of 6 to 26; and the polysaccharide represented by Formula (1) has at least one $—CH_2CH(OH)CH_2OC_jH_{2j+1}$.

9 Claims, No Drawings

ENDOSCOPIC SUBMUCOSAL INJECTION MATERIAL

CROSS-REFERENCE TO RELATED APPLICATION

This application is a Continuation of International Application No. PCT/JP2022/018074, filed Apr. 18, 2022, which claims priority to Japanese Patent Application No. 2021-100417, filed Jun. 16, 2021. Each of the above applications is hereby expressly incorporated by reference, in its entirety, into the present application.

BACKGROUND OF THE INVENTION

1. Field of the Invention

The present disclosure relates to an endoscopic submucosal injection material.

2. Description of the Related Art

Endoscopic mucosal resection (EMR) and endoscopic submucosal dissection (ESD) are known as treatment methods for gastrointestinal tract polyps, early gastric cancer, and early colorectal cancer.

In EMR or ESD, in order to facilitate resection, an endoscopic submucosal injection material is injected into a submucosal layer of a lesion area to elevate a mucous membrane below the lesion area.

For example, JP2001-192336A discloses an endoscopic submucosal injection material containing sodium hyaluronate.

In addition, JP2014-188054A discloses an endoscopic submucosal injection material containing sodium alginate.

In addition, JP2017-506208A discloses an endoscopic submucosal injection material containing carboxymethyl cellulose, hydroxypropyl ethyl cellulose, xanthan gum, or the like.

In addition, WO2013/077357A discloses an endoscopic submucosal injection material containing xanthan gum.

SUMMARY OF THE INVENTION

An endoscopic submucosal injection material is required to be excellent in elevation and elevation sustainability, but the elevation and the elevation sustainability are not sufficient in the endoscopic submucosal injection material disclosed in JP2001-192336A and JP2014-188054A, and there is room for improvement.

In addition, in the endoscopic submucosal injection material containing carboxymethyl cellulose or hydroxypropyl ethyl cellulose disclosed in JP2017-506208A, the elevation and the elevation sustainability are not sufficient, and also, a high pressure is required for the injection into the submucosal layer, and there is still room for improvement in ease of injection.

Because polysaccharides such as carboxymethyl cellulose and xanthan gum after synthesis may contain bacteria-derived impurities (endotoxin or the like), it is required to perform purification via a strong alkaline decomposition treatment, a filter filtration treatment, or the like before incorporation into an endoscopic submucosal injection material. In addition, the purification via a strong alkaline decomposition treatment is preferable because in the purification via a filter filtration treatment, the preparation of a device and the like raises the cost of manufacturing.

The endoscopic submucosal injection material disclosed in JP2017-506208A and WO2013/077357A contains xanthan gum, but because xanthan gum is denatured by a strong alkaline decomposition treatment, the endoscopic submucosal injection material cannot be obtained.

In addition, because an aqueous solution of xanthan gum has a high viscosity, it is required to dilute the above-mentioned aqueous solution in the case of carrying out a filter filtration treatment, and it is also required to adjust the concentration of the xanthan gum after the dilution.

Thus, regarding the endoscopic submucosal injection material disclosed in JP2017-506208A and WO2013/077357A, there is room for improvement in the manufacturing suitability of the endoscopic submucosal injection material.

The present disclosure has been made in view of the above-mentioned problems, and an object to be achieved thereof is to provide an endoscopic submucosal injection material which is excellent in elevation, elevation sustainability, ease of injection, and manufacturing suitability.

Specific means for achieving the object are as follows.

<1> An endoscopic submucosal injection material containing: water; and a polysaccharide represented by Formula (1).

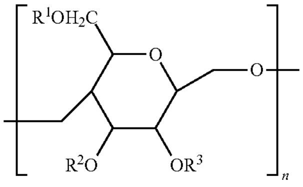

(1)

In Formula (1), $R^1$, $R^2$, and $R^3$ each independently represent a hydrogen atom, an alkyl group having 1 to 4 carbon atoms, $-[CH_2CH_{2-k}(CH_3)_kO]_mH$, or $-CH_2CH(OH)CH_2OC_jH_{2j+1}$; n represents an integer of 100 to 100,000; k represents 0 or 1; m represents an integer of 1 to 10; j represents an integer of 6 to 26; and the polysaccharide represented by Formula (1) has at least one $-CH_2CH(OH)CH_2OC_jH_{2j+1}$.

<2> The endoscopic submucosal injection material according to <1>, in which a ratio of a viscosity at a temperature of 25 °C and a frequency of 1 Hz to a viscosity at a temperature of 25 °C and a frequency of 100 Hz is 10 or more.

<3> The endoscopic submucosal injection material according to <1> or <2>, in which a viscosity at a temperature of 25 °C and a frequency of 100 Hz is 150 mPa·s or less.

<4> The endoscopic submucosal injection material according to any one of <1> to <3>, in which a viscosity at a temperature of 25 °C and a frequency of 1 Hz is 2,000 mPa·s or more.

<5> The endoscopic submucosal injection material according to any one of <1> to <4>, in which j is an integer of 10 to 20 in Formula (1).

<6> The endoscopic submucosal injection material according to any one of <1> to <5>, in which the polysaccharide includes stearylated hydroxypropyl methylcellulose.

<7> The endoscopic submucosal injection material according to any one of <1> to <6>, in which a content of $-CH_2CH(OH)CH_2OC_jH_{2j+1}$ with respect to a mass of the polysaccharide is 0.2% by mass to 1.0% by mass.

<8> The endoscopic submucosal injection material according to any one of <1> to <7>, in which a content of the polysaccharide with respect to a mass of the endoscopic submucosal injection material is 0.1% by mass to 0.5% by mass.

<9> The endoscopic submucosal injection material according to any one of <1> to <8>, further containing an organic compound having a molecular weight of 400 or less and having two or more hydroxyl groups.

<10> The endoscopic submucosal injection material according to <9>, in which a content of the organic compound with respect to a mass of the endoscopic submucosal injection material is 0.1% by mass or more.

According to the present disclosure, an endoscopic submucosal injection material which is excellent in elevation, elevation sustainability, ease of injection, and manufacturing suitability can be provided.

DESCRIPTION OF THE PREFERRED EMBODIMENTS

In the present disclosure, a numerical value range shown using "to" includes numerical values written before and after "to" as a minimum value and a maximum value, respectively.

In a numerical value range described in a stepwise manner in the present disclosure, an upper limit value or a lower limit value described in one numerical value range may be replaced with an upper limit value or a lower limit value in another numerical value range described in a stepwise manner. Furthermore, in a numerical value range described in the present disclosure, an upper limit value or a lower limit value of this numerical value range may be replaced with values shown in synthesis examples.

In the present disclosure, a viscosity of an endoscopic submucosal injection material is measured using a rheometer with a temperature of the endoscopic submucosal injection material set to 25 °C.

As the rheometer, it is possible to use a rheometer (manufactured by Anton Paar GmbH, automated rheometer MCR 102) to which a cone-plate jig (parallel plate, 10 mm (D) is attached, or to use a similar device thereof.

In the present disclosure, a weight-average molecular weight (Mw) is a value obtained by determining using the following GPC determination device under the following determination conditions and converting using a calibration curve of polystyrene standards. In addition, the calibration curve is created using five sample sets ("PStQuick MP-H" and "PStQuick B", manufactured by Tosoh Corporation) as polystyrene standards.

(GPC Determination Device)

GPC device: high speed GPC device "HCL-8320GPC", detector: differential refractometer or UV, manufactured by Tosoh Corporation Column: TSKgel SuperHZM-H, TSKgel SuperHZ4000, and TSKgel SuperHZ2000 (all manufactured by Tosoh Corporation) which are connected in series in this order and used (Determination Conditions)

Solvent: N-methylpyrrolidone (NMP)

Column temperature: 40 °C.

In the present disclosure, the content of an alkyl group having 1 to 4 carbon atoms, a content of $—[CH_2CH_{2-k}(CH_3)_k O]_mH$, and a content of $—CH_2CH(OH)CH_2OC_jH_{2j+1}$ with respect to a mass of a polysaccharide represented by Formula (1) are measured by a method according to the section of Hydroxypropyl Methylcellulose 2208 of the Japanese Pharmacopoeia 13th Edition.

<Endoscopic Submucosal Injection Material>

An endoscopic submucosal injection material according to the present disclosure contains the polysaccharide represented by Formula (1) and water.

(1)

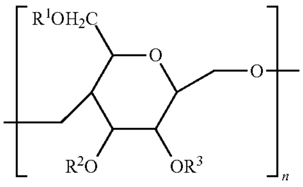

In Formula (1), $R^1$, $R^2$, and $R^3$ each independently represent a hydrogen atom, an alkyl group having 1 to 4 carbon atoms, $—[CH_2CH_{2-k}(CH_3)_kO]_mH$, or $—CH_2CH(OH)CH_2OC_jH_{2j+1}$; n represents an integer of 100 to 100,000; k represents 0 or 1; m represents an integer of 1 to 10; j represents an integer of 6 to 26; and the polysaccharide represented by Formula (1) has at least one $—CH_2CH(OH)CH_2OC_jH_{2j+1}$.

The endoscopic submucosal injection material according to the present disclosure is in excellent in elevation, elevation sustainability, ease of injection, and manufacturing suitability.

The reason why the above-mentioned effects are obtained is presumed as follows, but is not limited thereto.

The polysaccharide represented by Formula (1) contained in the endoscopic submucosal injection material of the present disclosure has $—CH_2CH(OH)CH_2OC_jH_{2j+1}$ (hereinafter, also referred to as a specific group). In an endoscopic submucosal injection material in a state where no force such as pressure is applied or a small force is applied, it is presumed that elevation and elevation sustainability are improved because polysaccharides are aggregated due to a hydrophobic interaction of specific groups.

In addition, it is presumed that, by the pressure applied to the endoscopic submucosal injection material during injection, the above-mentioned hydrophobic interaction is eliminated, which reduces the viscosity of the endoscopic submucosal injection material, thereby improving ease of injection.

Furthermore, it is presumed that the polysaccharide represented by Formula (1) has a cellulose ether skeleton and thus has excellent suitability for a strong alkaline decomposition treatment.

The viscosity of the endoscopic submucosal injection material at a temperature of 25 °C and a frequency of 100 Hz is preferably 200 mPa·s or less, more preferably 150 mPa·s or less, and further preferably 100 mPa·s or less. Since the above-mentioned viscosity is 200 mPa·s or less, ease of injection can further be improved.

The lower limit value of the above-mentioned viscosity is not particularly limited, but can be 10 mPa·s or more, for example.

The viscosity of the endoscopic submucosal injection material at a temperature of 25 °C and a frequency of 1 Hz is preferably 1,500 mPa·s or more, more preferably 2,000 mPa·s or more, and further preferably 2,500 mPa·s or more. Since the above-mentioned viscosity is 1,500 mPa·s or more, elevation and elevation sustainability can further be improved.

The upper limit value of the above-mentioned viscosity is not particularly limited, but can be 100,000 mPa·s or less, for example.

From the viewpoints of elevation, elevation sustainability, and ease of injection, a ratio of the viscosity of the endoscopic submucosal injection material at a temperature of 25 °C and a frequency of 1 Hz to the viscosity of the endoscopic submucosal injection material at a temperature of 25 °C and a frequency of 100 Hz is preferably 10 or more, more preferably 20 or more, further preferably 30 or more, and particularly preferably 35 or more.

From the viewpoint of safety, an osmotic pressure ratio of the endoscopic submucosal injection material to physiological saline is preferably 0.7 to 1.5.

In the present disclosure, the osmotic pressure is determined according to the 2.47 Osmolarity Determination (method for determining an osmotic concentration) of the Japanese Pharmacopoeia 17th Edition (Mar. 7, 2016, the Ministry of Health, Labour and Welfare Ministerial Notification No. 64) using an osmometer (manufactured by Gonotec GmbH, OSMOMAT 300 (D)) or a similar device thereof.

For physiological saline, OTSUKA NORMAL SALINE (manufactured by Otsuka Pharmaceutical Factory, Inc., osmotic pressure 288 mOsmol/kg) is used, and the osmotic pressure ratio is obtained by dividing the determined osmotic pressure by the osmotic pressure value of the OTSUKA NORMAL SALINE.

From the viewpoint of safety, the amount of endotoxin in the endoscopic submucosal injection material is preferably 0.1 EU/mL or less.

In the present disclosure, the amount of endotoxin is detected according to the gelling method of the Japanese Pharmacopoeia 17th Edition (Mar. 7, 2016, the Ministry of Health, Labour and Welfare Ministerial Notification No. 64). A Limulus Color KY Test Wako is used as an endotoxin detection reagent, and a Japanese Pharmacopoeia endotoxin reference standard is used as an endotoxin reference standard.

(Polysaccharide Represented by Formula (1))

In Formula (1), $R^1$, $R^2$, and $R^3$ each independently represent a hydrogen atom, an alkyl group having 1 to 4 carbon atoms, $—[CH_2CH_{2-k}(CH_3)_kO]_mH$, or $—CH_2CH(OH)CH_2OC_jH_{2j+1}$.

In addition, in a case where n is 2 or more, two or more $R^1$'s and the like may be the same as or different from each other.

The alkyl group having 1 to 4 carbon atoms may be linear or branched. Examples of the alkyl groups having 1 to 4 carbon atoms include a methyl group, an ethyl group, a propyl group, an isopropyl group, a butyl group, an isobutyl group, and t-butyl group.

The content of the alkyl group having 1 to 4 carbon atoms with respect to the mass of the polysaccharide represented by Formula (1) is preferably 10% by mass to 50% by mass.

In $—[CH_2CH_{2-k}(CH_3)_kO]_mH$, k represents 0 or 1. In addition, m represents an integer of 1 to 10, preferably an integer of 1 to 5, and more preferably 1.

The content of $—[CH_2CH_{2-k}(CH_3)_kO]_mH$ with respect to the mass of the polysaccharide represented by Formula (1) is preferably 3% by mass to 20% by mass.

In $—CH_2CH(OH)CH_2OC_jH_{2j+1}$, j represents an integer of 6 to 26, and from the viewpoint of elevation, elevation sustainability, and ease of injection, j preferably represents an integer of 10 to 20, and more preferably represents an integer of 15 to 18.

From the viewpoint of elevation, elevation sustainability, and ease of injection, the content of $—CH_2CH(OH)CH_2OC_jH_{2j+1}$ with respect to the mass of the polysaccharide represented by Formula (1) is preferably 0.1% by mass to 10% by mass, more preferably 0.2% by mass to 1.0% by mass, and further preferably 0.3% by mass to 0.6% by mass.

In Formula (1), n represents an integer of 100 to 100,000, preferably represents an integer of 100 to 10,000, and more preferably represents an integer of 2,000 to 4,000.

Mw of the polysaccharide represented by Formula (1) is preferably 10,000 to 10,000,000, more preferably 50,000 to 5,000,000, and further preferably 100,000 to 1,000,000.

Examples of the polysaccharides satisfying Formula (1) include palmitoylated hydroxypropyl methylcellulose, margarylated hydroxypropyl methylcellulose, and stearylated hydroxypropyl methylcellulose.

The polysaccharides satisfying Formula (1) preferably include stearylated hydroxypropyl methylcellulose from the viewpoint of elevation, elevation sustainability, and ease of injection.

From the viewpoint of elevation, elevation sustainability, and ease of injection, the content of the polysaccharide represented by Formula (1) with respect to the mass of the endoscopic submucosal injection material is preferably 0.1% by mass to 0.5% by mass, and more preferably 0.25% by mass to 0.35% by mass.

The endoscopic submucosal injection material may contain two or more types of the polysaccharide represented by Formula (1). The two or more types of the polysaccharide represented by Formula (1) may be structural isomers.

From the viewpoint of elevation, elevation sustainability, and ease of injection, the content of stearylated hydroxypropyl methylcellulose with respect to the total mass of the polysaccharides satisfying Formula (1) contained in the endoscopic submucosal injection material is preferably 50% by mass to 100% by mass, and more preferably 70% by mass to 100% by mass.

The polysaccharide satisfying Formula (1) may include two or more types of stearylated hydroxypropyl methylcellulose.

The polysaccharide represented by Formula (1) may be one manufactured by a conventionally known method or may be commercially available one.

Examples of commercially available products include SANGELOSE (registered trademark) 90L and SANGELOSE (registered trademark) 60L which are manufactured by Daido Chemical Corporation.

SANGELOSE (registered trademark) 90L and SANGELOSE (registered trademark) 60L are obtained by carrying out a strong alkaline decomposition treatment with a high-concentration sodium hydroxide aqueous solution (about 15% by mass to 40% by mass) when synthesizing stearylated hydroxypropyl methylcellulose. Specifically, the strong alkaline decomposition treatment is carried out by infusing cellulose with the high-concentration sodium hydroxide aqueous solution. Then, the cellulose (alkaline cellulose) after the strong alkaline decomposition treatment is used for synthesizing stearylated hydroxypropyl methylcellulose.

(Water)

Examples of the water include ion exchange water, pure water, and purified water, among which pure water or purified water is preferable from the viewpoint of the applicability to the endoscopic submucosal injection material.

In addition, purified water, in which sodium chloride to be described later, an organic compound, or the like has been dispersed or dissolved, or the like may be used.

The content of water with respect to the mass of the endoscopic submucosal injection material is not particularly limited, and can be 80% by mass to 99.9% by mass, for example.

(Organic Compound Having Molecular Weight of 400 or Less and Having Two or More Hydroxyl Groups)

The endoscopic submucosal injection material of the present disclosure may further contain an organic compound having a molecular weight of 400 or less and having two or more hydroxyl groups. When the endoscopic submucosal injection material contains the above-mentioned organic compound, the osmotic pressure of the endoscopic submucosal injection material can be adjusted.

The molecular weight of the above-mentioned organic compound is preferably 200 or less and more preferably 100 or less.

The lower limit value of the molecular weight of the above-mentioned organic compound is not particularly limited, but can be 50 or more, for example.

In the present disclosure, in a case where the organic compound is a monomer, the molecular weight of the organic compound having two or more hydroxyl groups and having a molecular weight of 400 or less is obtained from the chemical structure of the compound, and in a case where the organic compound is a polymerized substance such as an oligomer and a polymer, the molecular weight of the organic compound is determined using a GPC determination device under the same determination conditions as the determination of Mw.

Examples of the above-mentioned organic compounds include a glycol compound, a sugar alcohol compound, a monosaccharide compound, and a disaccharide compound, and the above-mentioned organic compound may include two or more types of these.

Examples of the glycol compounds include propylene glycol, triethylene glycol, and polyethylene glycol.

Examples of the sugar alcohol compounds include erythritol, glycerol, sorbitol, and xylitol.

Examples of the monosaccharide compounds include glucose, mannose, galactose, and fructose.

Examples of the disaccharide compounds include sucrose, lactose, lactulose, maltose, and trehalose.

The content of the organic compound with respect to the mass of the endoscopic submucosal injection material is preferably 0.1% by mass or more, and more preferably 0.2% by mass or more.

By setting the content of the above-mentioned organic compound within the above-mentioned numerical value range, the osmotic pressure ratio of the endoscopic submucosal injection material to physiological saline can be set to a favorable numerical value. The upper limit value of the content of the above-mentioned organic compound is not particularly limited, but can be 5% by mass or less, for example.

(Other)

The endoscopic submucosal injection material of the present disclosure may contain sodium chloride. When the endoscopic submucosal injection material contains sodium chloride, the osmotic pressure of the endoscopic submucosal injection material can be adjusted.

The content of the above-mentioned sodium chloride with respect to the mass of the endoscopic submucosal injection material is preferably within a range of 0.1% by mass to 5% by mass, and is more preferably within a range of 0.5% by mass to 1% by mass.

By setting the content of the above-mentioned sodium chloride within the above-mentioned numerical value range, the osmotic pressure ratio of the endoscopic submucosal injection material to physiological saline can be set to a favorable numerical value.

The endoscopic submucosal injection material may contain a polysaccharide other than the polysaccharide represented by Formula (1), and examples thereof include sodium hyaluronate, xanthan gum, sodium carboxymethyl cellulose, locust bean gum, dextran, dextrin, sodium alginate, hydroxyalkyl cellulose (such as hydroxypropyl ethyl cellulose), sodium carboxymethyl dextran, sodium poly(meth) acrylate, and polyvinyl alcohol.

The endoscopic submucosal injection material may contain a protein compound, and examples thereof include gelatin and casein.

Furthermore, the endoscopic submucosal injection material may contain a coloring agent, a contrast medium, a filling material, a cancer therapeutic agent, a hormone agent, an anti-inflammatory agent, an antibiotic, an analgesic drug, an antibacterial agent, a pH adjusting agent, or the like.

EXAMPLES

Hereinafter, the above-mentioned embodiment will be specifically described with reference to examples, but the above-mentioned embodiment is not limited to these examples.

Example 1

A 0.9% sodium chloride aqueous solution (manufactured by Hayashi Pure Chemical Ind., Ltd., 0.9 W/V % sodium chloride solution) was added to a polysaccharide A satisfying Formula (1) (manufactured by Daido Chemical Corporation, SANGELOSE (registered trademark) 90L; weight-average molecular weight: 700,000 to 900,000; content of $—CH_2CH(OH)CH_2OC_jH_{2j+1}$: 0.3% by mass to 0.6% by mass) to prepare an endoscopic submucosal injection material in which the content of the polysaccharide A was 0.3% by mass.

The SANGELOSE (registered trademark) 90L is a chemical which contains stearylated hydroxypropyl methylcellulose and from which impurities such as endotoxin have been removed by a strong alkaline decomposition treatment with a high-concentration sodium hydroxide aqueous solution when synthesizing stearylated hydroxypropyl methylcellulose.

As a result of detecting the amount of endotoxin in the endoscopic submucosal injection material according to the gelling method of the Japanese Pharmacopoeia 17th Edition (Mar. 7, 2016, the Ministry of Health, Labour and Welfare Ministerial Notification No. 64), the amount thereof was 0.0005 EU/mL or less (detection limit or less). A Limulus Color KY Test Wako was used as an endotoxin detection reagent, and a Japanese Pharmacopoeia endotoxin reference standard was used as an endotoxin reference standard.

Example 2 to Example 4

Endoscopic submucosal injection materials were prepared in the same manner as in Example 1 except that the content of the polysaccharide A was changed to the value shown in Table 1.

Example 5

An endoscopic submucosal injection material was prepared in the same manner as in Example 1 except that the polysaccharide A was changed to a polysaccharide B satisfying Formula (1) (manufactured by Daido Chemical Corporation, SANGELOSE (registered trademark) 60L; weight-average molecular weight: 300,000 to 500,000; content of $—CH_2CH(OH)CH_2OC_jH_{2j+1}$: 0.3% by mass to 0.6% by mass).

The SANGELOSE (registered trademark) 60L is a chemical which contains stearylated hydroxypropyl methylcellulose and from which impurities such as endotoxin have been removed by a strong alkaline decomposition treatment with a high-concentration sodium hydroxide aqueous solution when synthesizing stearylated hydroxypropyl methylcellulose.

Example 6

An endoscopic submucosal injection material was prepared in the same manner as in Example 1 except that glycerol (an organic compound having a molecular weight of 400 or less and having two or more hydroxyl groups) was further added such that the content thereof was 2.6% by mass.

Example 7

An endoscopic submucosal injection material was prepared in the same manner as in Example 1 except that the content of the polysaccharide A was changed to the value shown in Table 1, and that sodium carboxymethyl cellulose (a polysaccharide other than the polysaccharide represented by Formula (1), manufactured by Sigma-Aldrich Co., LLC.; weight-average molecular weight: 250,000) was further added such that the content thereof was 0.25% by mass.

Example 8

An endoscopic submucosal injection material in which the content of the polysaccharide A was 0.15% by mass and the content of the polysaccharide B was 0.15% by mass was prepared by adding a 0.9% sodium chloride aqueous solution (manufactured by Hayashi Pure Chemical Ind., Ltd., 0.9 W/V % sodium chloride solution) to the polysaccharide A and the polysaccharide B.

Comparative Example 1

An endoscopic submucosal injection material in which the content of sodium hyaluronate was 0.4% by mass was prepared by adding a 0.9% sodium chloride aqueous solution (manufactured by Hayashi Pure Chemical Ind., Ltd., 0.9 W/V % sodium chloride solution) to Hyaluronic Acid Sodium Salt (manufactured by FUJIFILM Wako Pure Chemical Corporation, sodium hyaluronate; weight-average molecular weight: 1,000,000).

Comparative Example 2

An endoscopic submucosal injection material was prepared in the same manner as in Comparative Example 1 except that the content of sodium hyaluronate was changed to the value shown in Table 1.

Comparative Example 3

An endoscopic submucosal injection material in which the content of sodium carboxymethyl cellulose was 0.5% by mass was prepared by adding a 0.9% sodium chloride aqueous solution (manufactured by Hayashi Pure Chemical Ind., Ltd., 0.9 W/V % sodium chloride solution) to Carboxymethyl Cellulose Sodium Salt (manufactured by FUJIFILM Wako Pure Chemical Corporation, sodium carboxymethyl cellulose).

Comparative Example 4

An endoscopic submucosal injection material in which the content of hydroxypropyl methylcellulose was 3.0% by mass was prepared by adding a 0.9% sodium chloride aqueous solution (manufactured by Hayashi Pure Chemical Ind., Ltd., 0.9 W/V % sodium chloride solution) to (Hydroxypropyl)methyl Cellulose (manufactured by Sigma-Aldrich Co., LLC.; Hydroxypropyl Cellulose 2.0-2.9; weight-average molecular weight: 120,000).

Comparative Example 5

An aqueous solution in which the content of unpurified Xanthan Gum (manufactured by FUJIFILM Wako Pure Chemical Corporation) was 0.6% by mass was prepared.

As a result of detecting the amount of endotoxin in the same manner as in Example 1, the amount thereof was 420 EU/mL.

As a result of making an attempt at subjecting the above-mentioned aqueous solution to a filter filtration treatment using an endotoxin removal filter (manufactured by Merck KGaA, Charged Durapore; pore diameter: 0.22 μm), the above-mentioned aqueous solution was not able to pass through the filter because of its high viscosity, and thus could not be used for preparing an endoscopic submucosal injection material.

In addition, as a result of subjecting the above-mentioned unpurified xanthan gum to the strong alkaline decomposition treatment with the high-concentration sodium hydroxide aqueous solution, the xanthan gum was confirmed to be denatured, and thus could not be used for preparing an endoscopic submucosal injection material.

Therefore, the subsequent measurement and evaluation were not carried out.

<Measurement of Viscosity>

The viscosity (hereinafter referred to as viscosity A) of the endoscopic submucosal injection materials prepared in the examples and the comparative examples was measured under the conditions of a frequency of 100 Hz and a temperature of 25 °C using a rheometer (manufactured by Anton Paar GmbH, automated rheometer MCR 102) to which a cone-plate jig (parallel plate, 10 mm (D) had been attached.

The viscosity (hereinafter referred to as viscosity B) of the endoscopic submucosal injection materials prepared in the examples and the comparative examples was measured under the condition of a temperature of 25 °C while changing the frequency to 1 Hz.

Furthermore, the ratio of the viscosity B to the viscosity A (viscosity B/viscosity A) was obtained.

These results are summarized in Table 1.

<Evaluation of Elevation>

An upper part (the upper part when the total length was divided into three equal parts) of an excised pig stomach was cut into a 5-cm square to produce a test piece.

2 mL of each of the endoscopic submucosal injection materials prepared in the examples and the comparative examples was injected into a submucosal layer of the test piece using an endoscopic puncture needle (manufactured by TOP Corporation, Super Grip; needle gauge: 23 G).

The height of the elevation of a mucosal layer immediately after the injection was measured and evaluated based on the following evaluation standards. The evaluation results are summarized in Table 1.

Regarding the measurement of the height of the elevation, the maximum height of the elevation was gauged using a laser displacement sensor IX-150 (manufactured by KEYENCE CORPORATION) with a built-in camera.

(Evaluation Standards)

A: The height of the elevation was 10 mm or more.

B: The height of the elevation was equal to or more than 8 mm and less than 10 mm.

C: The height of the elevation was equal to or more than 5 mm and less than 8 mm.

D: The height of the elevation was equal to or more than 2 mm and less than 5 mm.

E: The height of the elevation was less than 2 mm.

<Evaluation of Elevation Sustainability>

The upper part (the upper part when the total length was divided into three equal parts) of the excised pig stomach was cut into a 5-cm square to produce a test piece.

2 mL of each of the endoscopic submucosal injection materials prepared in the examples and the comparative examples was injected into the submucosal layer of the test piece using an endoscopic puncture needle (manufactured by TOP Corporation, Super Grip; needle gauge: 23 G).

The endoscopic submucosal injection material was injected into the test piece, and then left to stand for 30 minutes.

The height of the elevation of the mucosal layer after being left to stand was measured in the same manner as in the evaluation of the elevation, and was evaluated based on the following evaluation standards. The evaluation results are summarized in Table 1.

(Evaluation Standards)

A: The difference between the height of the elevation immediately after the injection and the height of the elevation after being left to stand for 30 minutes was less than 1 mm.

B: The difference in the height of the elevation was equal to or more than 1 mm and less than 2 mm.

C: The difference in the height of the elevation was 2 mm or more.

<Evaluation of Ease of Injection>

A syringe (manufactured by Terumo Corporation, Terumo Syringe 5 ml) filled with 5 mL of the endoscopic submucosal injection material prepared in each of the examples and the comparative examples was prepared.

The above-mentioned syringe was connected to an endoscopic puncture needle (manufactured by TOP Corporation, Super Grip; needle gauge: 23 G), and a plunger of the syringe was pressed at a rate of 100 mm/minute to measure the maximum load when pressing using a tension tester (manufactured by A&D Company, Limited, Table Top Universal Testing Machine (Force Tester) MCT-2150). The measured maximum load was evaluated based on the following evaluation standards. The evaluation results are summarized in Table 1.

(Evaluation Standards)

A: The maximum load was less than 25 N.

B: The maximum load was equal to or more than 25 N and less than 50 N.

C: The maximum load was equal to or more than 50 N and less than 75 N.

D: The maximum load was equal to or more than 75 N and less than 100 N.

E: The maximum load was 100 N or more.

TABLE 1

| | Composition (% by mass) | | | | | | | | | Evaluation | | |
|---|---|---|---|---|---|---|---|---|---|---|---|---|
| | Polysaccharide A | Polysaccharide B | Glycerol | Sodium carboxy methyl cellulose | Sodium hyaluronate | Hydroxypropyl methylcellulose | Viscosity A (mPa · s) | Viscosity B (mPa · s) | Viscosity B/ Viscosity A | Evaluation of elevation | Evaluation of elevation sustainability | Evaluation of ease of injection |
| Example 1 | 0.3 | — | — | — | — | — | 95 | 2800 | 29.4 | A | A | A |
| Example 2 | 0.2 | — | — | — | — | — | 42 | 1800 | 42.9 | A | B | A |
| Example 3 | 0.25 | — | — | — | — | — | 60 | 2400 | 39.2 | A | A | A |
| Example 4 | 0.4 | — | — | — | — | — | 171 | 5700 | 33.3 | A | A | B |
| Example 5 | — | 0.3 | — | — | — | — | 78 | 1800 | 23.1 | B | B | A |
| Example 6 | 0.3 | — | 2.6 | — | — | — | 96 | 2600 | 27.0 | A | A | A |
| Example 7 | 0.15 | — | — | 0.25 | — | — | 125 | 1600 | 12.8 | B | B | B |
| Example 8 | 0.15 | 0.15 | — | — | — | — | 145 | 5200 | 35.8 | A | A | A |
| Comparative Example 1 | — | — | — | — | 0.4 | — | 49 | 88 | 1.8 | C | C | B |
| Comparative Example 2 | — | — | — | — | 0.8 | — | 196 | 352 | 1.8 | C | B | C |
| Comparative Example 3 | — | — | — | 0.5 | — | — | 170 | 860 | 5.1 | C | C | C |
| Comparative Example 4 | — | — | — | — | — | 3.0 | 226 | 404 | 1.8 | D | C | D |

From the results of Table 1, it was found that the endoscopic submucosal injection materials prepared in the examples were excellent in elevation, elevation sustainability, and ease of injection, as compared to the endoscopic submucosal injection materials prepared in Comparative Example 1 to Comparative Example 4.

In addition, it was found that the endoscopic submucosal injection material could not be prepared in Comparative Example 5 because the xanthan gum was denatured by the strong alkaline decomposition treatment, and also, the aqueous solution containing the xanthan gum could not be subjected to the filter filtration treatment; whereas the polysaccharide A and the polysaccharide B, which satisfy Formula (1) and which were contained in the endoscopic submucosal injection materials prepared in the examples, were subjected to the strong alkaline decomposition treatment, making manufacturing suitability excellent.

The entire content of the disclosure of Japanese Patent Application No. 2021-100417 filed Jun. 16, 2021 is incorporated in the present specification by reference. All documents, patent applications, and technical standards described in the present specification are incorporated in the present specification by reference such that each of the documents, the patent applications, and the technical standards is incorporated by reference to the same extent as the case in which each thereof is specifically and individually described.

What is claimed is:

1. An endoscopic submucosal injection material comprising:

water; and a polysaccharide represented by Formula (1):

(1)

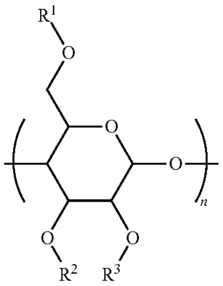

wherein in Formula (1), $R^1$, $R^2$, and $R^3$ each independently represent a hydrogen atom, an alkyl group having 1 to 4 carbon atoms, $—[CH_2CH_{2-k}(CH_3)_kO]_mH$, or $—CH_2CH(OH)CH_2OC_jH_{2j+1}$; n represents an integer of 100 to 100,000; k represents 0 or 1; m represents an integer of 1 to 10; j represents an integer of 6 to 26; and the polysaccharide represented by Formula (1) has at least one $—CH_2CH(OH)CH_2OC_jH_{2j+1}$, wherein an osmotic pressure ratio of the endoscopic submucosal injection material to physiological saline is 0.7 to 1.5, and wherein a ratio of a viscosity at a temperature of 25 °C and a frequency of 1 Hz to a viscosity at a temperature of 25 °C and a frequency of 100 Hz is 10 or more.

2. The endoscopic submucosal injection material according to claim 1, wherein the viscosity at a temperature of 25 °C and a frequency of 100 Hz is 150 mPa·s or less.

3. The endoscopic submucosal injection material according to claim 1, wherein the viscosity at a temperature of 25 °C and a frequency of 1 Hz is 2,000 mPa·s or more.

4. The endoscopic submucosal injection material according to claim 1, wherein j is an integer of 10 to 20 in Formula (1).

5. The endoscopic submucosal injection material according to claim 1, wherein the polysaccharide includes stearylated hydroxypropyl methylcellulose.

6. The endoscopic submucosal injection material according to claim 1, wherein a content of $—CH_2CH(OH)CH_2OC_jH_{2j+1}$ with respect to a mass of the polysaccharide is 0.2% by mass to 1.0% by mass.

7. The endoscopic submucosal injection material according to claim 1, wherein a content of the polysaccharide with respect to a mass of the endoscopic submucosal injection material is 0.1% by mass to 0.5% by mass.

8. The endoscopic submucosal injection material according to claim 1, further comprising:

an organic compound having a molecular weight of 400 or less and having two or more hydroxyl groups.

9. The endoscopic submucosal injection material according to claim 8, wherein a content of the organic compound with respect to a mass of the endoscopic submucosal injection material is 0.1% by mass or more.

* * * * *